United States Patent [19]

Chiu et al.

[11] Patent Number: 5,420,322

[45] Date of Patent: May 30, 1995

[54] PREPARATION OF ALKALI-METAL HEXAMETHYDISILAZANES

[75] Inventors: Kuen-Wai Chiu, Wexford; David H. Ellenberger, Fenelton; Joseph M. Barendt, Mars, all of Pa.

[73] Assignee: Mine Safety Appliances Company, Pittsburgh, Pa.

[21] Appl. No.: 298,831

[22] Filed: Aug. 31, 1994

[51] Int. Cl.$^6$ ............................................. C07F 7/10
[52] U.S. Cl. ................................................. 556/412
[58] Field of Search .......................................... 552/412

[56] References Cited

U.S. PATENT DOCUMENTS 4,659,850 4/1987 Arai et al. ................. 556/412 X
4,882,448 11/1989 Vaahs ................................ 556/412

Primary Examiner—Paul F. Shaver
Attorney, Agent, or Firm—Henry E. Bartony, Jr.; James G. Uber

[57] ABSTRACT

A one-step synthesis of an alkali-metal hexamethyldisilazane is provided in which an alkali metal selected from the group consisting of lithium, sodium and potassium is reacted with 1,1,1,3,3,3,-hexamethyldisilazane at a reaction temperature above the melting point of the alkali metal without the use of an electron carrier, alkali-metal derivatized reagents, such as alkyl-aryl organometals, alkali-metal amides and alkali-metal hydrides, or a catalyst.

18 Claims, No Drawings

PREPARATION OF ALKALI-METAL HEXAMETHYDISILAZANES

FIELD OF THE INVENTION

The present invention relates to a method for the production of alkali-metal hexamethyldisilazanes, and especially to a method of synthesizing alkali-metal hexamethyldisilazanes directly from alkali metals.

BACKGROUND OF THE INVENTION

Alkali-metal hexamethyldisilazanes have been prepared from hexamethyldisilazane (HN[Si(CH$_3$)$_3$]$_2$ or HMDS) under a number of synthetic schemes. However, each of these synthetic schemes has one or more significant drawbacks associated therewith.

Under one such synthetic scheme, alkali-metal hexamethyldisilazanes are prepared using organometallic reagents such as n-butyllithium, phenyllithium, phenylsodium and phenylpotassium. An example of such a reaction using n-butyllithium to produce lithium hexamethyldisilazane is provided below:

n-BuLi+HN[Si(CH$_3$)$_3$]$_2$→LiN[-Si(CH$_3$)$_3$]$_2$+CH$_3$CH$_2$CH$_2$CH$_3$ ↑

Such organometallic reagents are generally pyrophoric, however, and thus create tremendous material handling problems.

Alkali-metal hexamethyldisilazanes are also prepared using alkali-metal amides or alkali-metal hydride reagents at room temperature as shown below:

LiH+HN[Si(CH$_3$)$_3$]$_2$→LiN[Si(CH$_3$)$_3$]$_2$+H$_2$ ↑

LiNH$_2$+HN[Si(CH$_3$)$_3$]$_2$LiN[Si(CH$_3$)$_3$]$_2$+NH$_3$ ↑

Reactions of alkali-metal amides or alkali-metal hydride and hexamethyldisilazane generally do not proceed to completion, however, and result in the formation of entrapped, unreacted amides or hydrides which can give rise to undesirable by-products and safe-handling problems.

Lithium diisopropylamide (LDA) has been produced directly from lithium metal using an electron carrier such as styrene or isoprene in THF as follows:

Li + HN(CH(CH$_3$)$_2$)$_2$ $\xrightarrow{\text{THF}}_{\text{Styrene}}$

LiN(CH(CH$_3$)$_2$)$_2$ + ½CH$_3$CH$_2$C$_6$H$_5$

See U.S. Pat. No. 4,595,779. Suitable electron carriers are conjugated, unsaturated hydrocarbons. These electron carriers are noted to readily accept electrons from an alkali metal to form free radicals or carbanions.

However, the use of electron carriers such as styrene in such reactions usually results in formation of toxic alkylbenzene side products and necessitates difficult separation of the product.

It is very desirable to develop a synthetic scheme for the production of alkali-metal hexamethyldisilazanes that does not suffer from the drawbacks associated with the above synthetic schemes.

SUMMARY OF THE INVENTION

Accordingly, the present invention provides a method for the synthesis of alkali-metal hexamethyldisilazanes directly from alkali metals and hexamethyldisilazane that substantially avoids the drawbacks associated with prior synthetic schemes.

In general, the present invention provides a method for a one-step synthesis of an alkali-metal hexamethyldisilazane comprising the step of reacting an alkali metal selected from the group consisting of lithium, sodium and potassium with 1,1,1,3,3,3-hexamethyldisilazane at a temperature above the melting point of the alkali metal without the use of an electron carrier reagent. The problems and expense associated with electron carrier reagents are thereby avoided.

Moreover, as the alkali -metal hexamethyldisilazanes (M[NSi(CH$_3$)$_3$)]$_2$ or MHMDS, wherein M is an alkali metal selected from the group of Li, Na or K) are synthesized directly from alkali metals and HMDS, the present invention eliminates the need to prepare alkali-metal derivative reagents such as alkyl and phenyl organometals, alkali-metal amides or alkali-metal hydrides. Therefore, the present synthetic scheme (i) is less expensive than prior synthetic schemes using alkali-metal derivatized reagents and (ii) avoids the technical problems associated with the use of alkali-metal derivatized reagents.

DETAILED DESCRIPTION OF THE INVENTION

It has been discovered that alkali-metal hexamethyldisilazanes can be synthesized directly from alkali metals and 1,1,1,3,3,3-hexamethyldisilazane at temperatures above the melting points of the alkali metals without the use of an electron carrier reagent according to the following equation:

M+HN[Si(CH$_3$)$_3$]$_2$→MN[Si(CH$_3$)$_3$]$_2$+½H$_2$ ↑

In this reaction, the reaction pressure is preferably maintained sufficiently high to sustain the total vapor pressure at the reaction temperature. Either the alkali metal or 1,1,1,3,3,3-hexamethyldisilazane reagent can be used in excess and reaction may proceed with or without the use of solvents.

If a solvent or solvents are used in the present reaction, the preferred solvents include ethers, hydrocarbons and mines. Suitable ether solvents can be represented by the general formula R$^1$OR$^2$, wherein R$^1$ and R$^2$ are preferably independently selected from an alkyl group, an aryl group or an alkoxy group containing from 1 to 12 carbon atoms. Preferred ether solvent include butyl ether, tetrahydrofuran, monoglyme, diglyme and triglyme.

Suitable amine solvents include primary amines, secondary amines and tertiary amines, which can be represented respectively by the following general formula: R$^3$R$^4$R$^5$N. In this general formula, R$^3$, R$^4$, and R$^5$ are preferably independently selected from hydrogen, an alkyl group, an aryl group or an alkoxy group, such groups containing from 1 to 12 carbon atoms. Alternatively, R$^3$ and R$^4$ together can form an alkylene group containing from 1 to 8 carbon atoms. Suitable alkyl, aryl, alkoxy and alkylene groups may be substituted or unsubstituted. For example, R$^3$ and R$^4$ may be selected to be hydrogen and R$^5$ selected to be an amino-substituted propyl group (H$_2$NCH$_2$CH$_2$CH$_2$—) to provide 1,3-diaminopropane (1,3-DAP). Preferred amine solvents include hexylamine, 1,3-DAP, triethylamine and HMDS.

As used herein, the term hydrocarbon solvents refers to alkyl and aryl hydrocarbon solvents. Suitable alkyl hydrocarbons include straight chain, branched chain, saturated and unsaturated hydrocarbons containing from 1 to 12 carbon atoms. Suitable aryl hydrocarbons include phenyl hydrocarbons and alkyl substituted phenyl hydrocarbons. Preferred hydrocarbon solvents include toluene, xylene and cumene.

The most preferred solvents for use in the present invention include tetrahydrofuran, butyl ether, monoglyme, diglyme, triglyme, toluene, xylene, cumene, hexylamine, 1,3-DAP, triethylamine and HMDS. The reagent HMDS performs well as a solvent when present in excess.

Although not generally necessary, a catalyst may be used in the present reactions. If a catalyst is used, the preferred catalysts are transition metal salts. The most preferred catalyst is iron chloride (FeCl$_3$).

The melting points of Li, K and Na are approximately 180.54° C., 63.65° C. and 97.81° C., respectively. Although the present reactions may proceed at temperatures slightly in excess of the relevant melting points, the reactions proceed relatively slowly at such temperatures. In general, a greater reaction temperature requires shorter reaction time for the reaction to proceed to completion.

In the reaction of lithium and HMDS under the present invention, for example, the reaction temperature is preferably greater than or equal to approximately 190° C. More preferably, the reaction temperature is greater than or equal to approximately 215° C. At reaction temperatures between approximately 190° C. and 215° C., a catalyst comprising a transition metal salt is preferably used. Most preferably, the catalyst is iron chloride. Most preferably, the reaction temperature is greater than or equal to approximately 225° C. At a reaction temperature of approximately 225° C., the reaction is preferably allowed to proceed for approximately 12 to 24 hours. More preferably, the reaction time is between 16 to 24 hours.

If a solvent is used in the reaction of lithium and HMDS, the solvent must be chosen to be stable at the reaction temperature. Solvents suitable for use in the present reactions at temperatures above 190° C. include toluene, xylene, butyl ether and HMDS. Preferably, the reagent HMDS acts as the solvent (i.e., HMDS is used in excess) in the reaction of lithium and HMDS.

At a reaction temperature of approximately 225° C., a reaction pressure of at least approximately 90 psig is sufficient for the present reaction under reflux of solvent.

In the reaction of sodium and HMDS under the present invention, the reaction temperature is preferably greater than or equal to approximately 190° C. More preferably, the reaction temperature is greater than or equal to approximately 215° C. Most preferably, the reaction temperature is greater than or equal to approximately 225° C. At a reaction temperature of approximately 225° C., the reaction is preferably allowed to proceed for approximately 16 to 24 hours.

The preferred solvents for the reaction of sodium and HMDS are as discussed for the reaction of lithium and HMDS. HMDS is the most preferred solvent.

In the reaction of potassium and HMDS under the present invention, the reaction temperature is preferably greater than or equal to approximately 100° C. At a reaction temperature between approximately 64° C. and 100° C. a catalyst is preferably used. Preferably the catalyst is a transition metal salt. Most preferably the catalyst is iron salt such as iron chloride.

Preferably, a solvent is used in connection with the reaction to form potassium hexamethyldisilazane as it is difficult to achieve a complete reaction in the absence of a solvent. Although HMDS may be use as the solvent (used in a stoichiometric excess), it is preferable to use a solvent other than PIMDS which is more easily separated from the product than HMDS. Use of a solvent other than KMDS enables the use of a stoichiometric quantity of PIMDS and reduces the manufacturing costs.

The lower preferred reaction temperatures used in connection with potassium (as compared to lithium and sodium) enable the use of a number of solvents unsuitable for use at the preferred elevated temperatures of the lithium and sodium reactions discussed above. Preferred solvents for use in the reaction of potassium and HMDS include THF and toluene.

However, care must be taken with certain solvents to avoid decomposition during the reaction. When THF is used as a solvent, the reaction temperature is preferably kept in the range of approximately 100° C. to 140° C. More preferably, the reaction temperature is preferably kept in the range of approximately 100° C. to 135° C. Most preferably, the reaction temperature is preferably kept in the range of approximately 120° C. to 135° C.

When toluene is used as a solvent, the reaction temperature is preferably kept in the range of approximately 100° C. to 200° C., and more preferably in the range of approximately 100° C. to 180° C.

At a reaction temperature of 100° C. for the reaction of potassium and HMDS, the reaction time is preferably in the range of approximately 12 to 24 hours. At a reaction temperature of 120° C., the reaction time is preferably in the range of approximately 4 to 8 hours. At a reaction temperature of 135° C., the reaction time is preferably in the range of approximately 3 to 6 hours.

Higher reaction temperatures can be used for the reaction of potassium and PSfDS with appropriate choice of solvent. As described above, for example, HMDS or butyl ether can be used as solvents at elevated temperature.

EXAMPLES

The following representative experiments were carried out in a Parr-pressure-reactor equipped with a high-speed dispersing impeller. For the preparation of each alkali-metal hexamethyldisilazane, one or more detailed examples and a table summarizing several examples are set forth. Unless otherwise indicated, the reactions proceeded substantially to completion within the reaction time set forth.

Preparation of Lithium Hexamethyldisilazane

Example 1

To 288 ml of hexamethyldisilazane (220 g, 1.36 mole) in a 1-liter Parr reactor was charged 7.00 g of lithium metal (1.00 mole) under an argon atmosphere, with a backpressure of approximately 150 psig. The mixture was slowly heated to 225° C. over a 1 to 2 hour period. At this temperature and pressure, the reaction was allowed to proceed for approximately 16 hours with stirring and venting of hydrogen. The reaction mixture was then cooled to below 40° C. and hexane solvent (300 ml) was added to dissolve the product. Filtration to remove any unreacted lithium metal followed by evaporation under vacuum (2 mm Hg) at 110° C. provided approximately 150 g of lithium hexamethyldisilazane solid (approximately 0.90 mole, >90% yield, total base analysis: 101.3% of the theoretical value).

Example 2

To 220 ml of hexamethyldisilazane (168 g, 1.04 mole) were charged 7.30 g of lithium metal (1.05 mole) and a ferric chloride catalyst (0.07 g, 0.00043 mole). The mixture was heated to 190° C. After stirring for approximately 5 hours at 190° C., the reaction was found to be 20% complete (total base analysis: 100.3%).

Several experiments over a range of conditions for the reaction of lithium and HMDS are summarized in Table 1 below.

TABLE 1

| Reagents | Solvent or Co-solvent | Catalyst | Reaction Temp. (°C.) | Reaction Time (Hours) | Comments |
|---|---|---|---|---|---|
| Excess HMDS, Li | | None | 225 | 20 | Complete reaction |
| Excess HMDS, Li | | None | 225 | 16 | Complete reaction |
| HMDS, Butyl-Li | Hexane | None | 20 | 16 | Complete reaction |
| Excess HMDS, Li | | None | 225 | 16 | Complete reaction |
| Excess HMDS, Li | Hexyl-amine | None | 225 | 16 | Complete reaction |
| Excess HMDS, Li | 1,3-DAP | None | 225 | 16 | Complete reaction |
| Excess HMDS, Li | 1,3-DAP | FeCl$_3$ | 225 | 18 | Complete reaction |
| Excess HMDS, Li | EDA | FeCl$_3$ | 200 | 3 | Evidence that EDA decomposed |
| Excess HMDS, Li | | FeCl$_3$ | 190 | 5 | 20% complete |
| Excess HMDS, Li | | None | 190 | 20 | No reaction observed |
| Excess HMDS, Li | | None | 225 THF added at 120 | 16 | Evidence of decomposition on adding THF |
| HMDS, Excess Li | p-xylene | None | 225 | 20 | 45% complete |
| HMDS, Excess Li | butyl ether | None | 225 | 20 | 24% complete |

Preparation of Sodium Hexamethyldisilazane

Example 1

To 288 ml of hexamethyldisilazane (220 g, 1.36 mole) in a 1-liter Parr reactor under nitrogen was charged 15.0 g sodium metal (0.652 mole). The reaction mixture was heated to 225° C. over a one hour period and subsequently stirred at this temperature for approximately 24 hours. Following the procedure set forth in Example (1) for the preparation of lithium hexamethyldisilazane, the total free base analysis upon the dry sodium hexamethyldisilazane powder was 100%. The yield was quantitative.

Several experiments over a range of conditions for the reaction of sodium and HMDS are summarized in Table 2 below.

TABLE 2

| Reagents | Solvent or Co-solvent | Catalyst | Reaction Temp. (°C.) | Reaction Time (Hours) | Comments |
|---|---|---|---|---|---|
| Excess HMDS, Na | | None | 225 | 24 | Complete reaction |
| HMDS, Excess Na | xylene | None | 225 | 20 | 30% complete |
| HMDS, Excess Na | butyl ether | None | 225 | 20 | 65% complete |
| HMDS, Excess Na | butyl ether | None | 250 | 20 | 72% complete trace decomposition |

Preparation of Potassium Hexamethyldisilazane

Example 1

To 306 ml of THF were charged 73.5 ml hexamethyldisilazane (56.3 g, 0.349 mole) and 13.4 g potassium metal (0.343 mole) in a Parr reactor under nitrogen. The reaction mixture was heated to 120° C. over a one hour period and stirred at that temperature for approximately 8 hours. After this period, heating was ceased and the reaction mixture was allowed to cool to room temperature. Filtration and vacuum removal of volatile components gave a white potassium hexamethyldisilazane powder in quantitative yield with free base analysis of 99.39% and KOH/K$_2$CO$_3$ contents of 0.79%.

Example 2

In this experiment, the procedure of Example (1) was repeated at higher temperature (that is, at 140° C. rather than 120° C.). To 260 ml THF were charged 70.0 ml hexamethyldisilazane (53.5 g, 0.331 mole) and 13.4 g potassium metal (0.343 mole). The reaction mixture was stirred at 140° C. for approximately 6 hr. Following the procedure of Example (1), a brown potassium hexamethyldisilazane powder was obtained with free base analysis of only 91.43% and KOH/K$_2$CO$_3$ contents of 4.22%. These data indicated that the potassium hexamethyldisilazane in THF decomposed under the above reaction conditions.

Example 3

In this experiment, the procedure of Example (1) was repeated using a different solvent system (that is, using toluene as the solvent in place of THF). To 438 ml of toluene were charged 70.0 ml of hexamethyldisilazane (53.5 g, 0.331 mole) and 13.4 g of potassium metal (0.343 mole). The reaction mixture was heated to 140° C. and stirred at this temperature for approximately 6 hours. Following the procedure of Example (1), a white potassium hexamethyldisilazane powder was obtained in quantitative yield with free base analysis of 98.8% and KOH/K$_2$CO$_3$ contents of 1.43%.

Example 4

In this experiment, the procedure of Example (3) was repeated at 225° C. rather than 140° C. After a 5 hour reaction time, the Parr reactor was cooled to room temperature and opened under nitrogen inside a drybox. The potassium hexamethyldisilazane product was found to be decomposed as a green-colored material insoluble in the toluene solvent.

Several experiments over a range of conditions for the reaction of potassium and HIDS are summarized in Table 3 below.

TABLE 3

| Reagents | Solvent or Co-solvent | Catalyst | Reaction Temp. (°C.) | Reaction Time (Hours) | Comments |
|---|---|---|---|---|---|
| Excess HMDS, K | THF | None | 120 | 8 | complete reaction |
| HMDS, K | THF | None | 120 | 6 | complete reaction |
| HMDS, Excess K | THF | None | 120 | 6 | complete reaction |
| Excess HMDS, K | THF | None | 120 | 5 | complete reaction |
| HMDS, Excess K | THF | None | 140 | 6 | brown powder evidencing decomposition |
| HMDS, Excess K | Toluene | None | 140 | 20 | complete reaction |
| HMDS, Excess K | Toluene | None | 140 | 6 | complete reaction |
| HMDS, Excess K | Toluene | FeCl$_3$ | 140 | 5 | complete reaction |
| Large Excess HMDS, K | | None | 140 | 5 | complete reaction |
| Excess HMDS, K | | None | 200 | 4 | complete reaction (white crystal) |
| HMDS, Excess K | Toluene | None | 225 | 5 | green color evidencing decomposition |
| HMDS, Excess K | Toluene | None | 180 | 6 | complete reaction slight decomposition |

Although, the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method for a one-step synthesis of an alkali-metal hexamethyldisilazane comprising the step of reacting an alkali metal selected from the group consisting of lithium, sodium and potassium with 1,1,1,3,3,3,-hexamethyldisilazane at a reaction temperature greater that the melting point of the alkali metal without the use of an electron carrier reagent.

2. The method of claim 1 wherein the alkali metal is lithium and the reaction temperature is at least approximately 190° C.

3. The method of claim 2 wherein the reaction temperature is at least approximately 225° C.

4. The method of claim 1 wherein the alkali metal is sodium and the reaction temperature is at least 190° C.

5. The method of claim 4 wherein the reaction temperature is at least approximately 225° C.

6. The method of claim 1 wherein the alkali metal is potassium and the reaction temperature is at least 100° C.

7. The method of claim 6 wherein the reaction takes place in a solvent.

8. The method of claim 7 wherein the solvent is selected from the group consisting of toluene and tetrahydrofuran.

9. The method of claim 8 wherein the solvent is tetrahydrofuran and the reaction temperature is no greater than approximately 140° C.

10. The method of claim 8 wherein the solvent is toluene and the reaction temperature is no greater than approximately 200° C.

11. The method of claim 3 wherein the reaction takes place in a solvent.

12. The method of claim 11 wherein the solvent is selected from the group consisting of hexylamine, 1,3-diaminopropane, butyl ether, toluene, xylene, cumene and 1,1,1,3,3,3,-hexamethyldisilazane.

13. The method of claim 5 wherein the reaction takes place in a solvent.

14. The method of claim 13 wherein the solvent is selected from the group consisting of hexylamine, 1,3-diaminopropane, butyl ether, toluene, xylene, cumene and 1,1,1,3,3,3,-hexamethyldisilazane.

15. The method of claim 1 wherein the reaction takes place in a solvent selected from the group consisting of an ether, a hydrocarbon and an amine.

16. The method of claim 15 wherein the solvent is selected from the group consisting of tetrahydrofuran, butyl ether, monoglyme, diglyme, triglyme, toluene, xylene, cumene and 1,1,1,3,3,3, -hexamethyldisilazane.

17. The method of claim 3 wherein excess 1,1,1,3,3,3,-hexamethyldisilazane is used.

18. The method of claim 5 wherein excess 1,1,1,3,3,3,-hexamethyldisilazane is used.

* * * * *